(12) United States Patent
Cory

(10) Patent No.: US 7,212,865 B2
(45) Date of Patent: May 1, 2007

(54) NERVE STIMULATOR AND METHOD

(76) Inventor: Philip Cory, 15075 Dell Rd., Bozeman, MT (US) 59715

( * ) Notice: Subject to any disclaimer, the term of this patent is extended or adjusted under 35 U.S.C. 154(b) by 359 days.

(21) Appl. No.: 10/853,590

(22) Filed: May 25, 2004

(65) Prior Publication Data

US 2005/0267545 A1   Dec. 1, 2005

(51) Int. Cl.
*A61N 1/00* (2006.01)

(52) U.S. Cl. ..................................................... 607/46

(58) Field of Classification Search .............. 607/2, 607/46, 47, 68, 71; 606/32, 41
See application file for complete search history.

(56) References Cited

U.S. PATENT DOCUMENTS

| | | | |
|---|---|---|---|
| 4,299,230 A | 11/1981 | Kubota | |
| 4,515,168 A | 5/1985 | Chester et al. | |
| 4,541,432 A * | 9/1985 | Molina-Negro et al. | 607/46 |
| 4,924,880 A * | 5/1990 | O'Neill et al. | 607/47 |
| 5,305,746 A | 4/1994 | Fendrock | |
| 5,306,236 A | 4/1994 | Blumenfeld et al. | |
| 5,320,109 A | 6/1994 | Chamoun et al. | |
| 5,358,514 A | 10/1994 | Schulman et al. | |
| 5,368,041 A | 11/1994 | Shambroom | |
| 5,381,804 A | 1/1995 | Shambroom | |
| 5,389,069 A | 2/1995 | Weaver | |
| 5,725,514 A | 3/1998 | Grinblat et al. | |
| 5,741,216 A | 4/1998 | Hemmingsen et al. | |
| 5,830,151 A | 11/1998 | Hadzic et al. | |
| 5,853,373 A * | 12/1998 | Griffith et al. | 600/554 |
| 5,993,434 A | 11/1999 | Dev et al. | |
| 6,009,347 A | 12/1999 | Hofmann | |
| 6,032,064 A | 2/2000 | Devlin et al. | |
| 6,032,072 A | 2/2000 | Greenwald et al. | |
| 6,269,270 B1 * | 7/2001 | Boveja | 607/45 |
| 6,298,256 B1 | 10/2001 | Meyer | |
| 6,325,764 B1 | 12/2001 | Griffith et al. | |
| 6,391,005 B1 | 5/2002 | Lum et al. | |
| 6,394,953 B1 | 5/2002 | Devlin et al. | |
| 6,434,410 B1 | 8/2002 | Cordero et al. | |
| 6,493,588 B1 * | 12/2002 | Malaney et al. | 607/46 |
| 6,599,281 B1 | 7/2003 | Struys et al. | |
| 6,605,072 B2 | 8/2003 | Struys et al. | |
| 6,654,626 B2 | 11/2003 | Devlin et al. | |
| 6,706,016 B2 | 3/2004 | Cory et al. | |
| 2003/0006782 A1 | 1/2003 | Shambroom et al. | |
| 2003/0036744 A1 | 2/2003 | Struys et al. | |
| 2003/0045858 A1 | 3/2003 | Struys et al. | |
| 2003/0052775 A1 | 3/2003 | Shambroom et al. | |
| 2003/0181821 A1 | 9/2003 | Greenwald et al. | |
| 2004/0015091 A1 | 1/2004 | Greenwald et al. | |
| 2005/0171576 A1 * | 8/2005 | Williams et al. | 607/48 |

OTHER PUBLICATIONS

Professional Instruments internal Memorandum and attached product description for DualStim Audio Model NS-2CA.

* cited by examiner

*Primary Examiner*—Robert E. Pezzuto
*Assistant Examiner*—Brian T. Gedeon

(57) ABSTRACT

This invention presents a device, and the method it implements, which is an improvement in the design of nerve stimulators. Like conventional stimulators, it uses a percutaneous, insulated needle for the performance of therapeutic interventions targeting nerves. The improvement comprises offering an option for either constant current or constant voltage, offering a choice of waveform parameters, controlling a pulse generator, supplying a second background waveform, measuring the current and voltage applied to the tissue, computing further electrical characteristics, dynamically adjusting circuit components to ensure a desirable waveform applied to the tissue, and displaying measured and computed electrical characteristics of the tissue. The object is improved positioning of a needle tip near a nerve or nerve plexus for regional anesthesia, pain management, and other medical purposes.

48 Claims, 4 Drawing Sheets

NERVE STIMULATOR AND METHOD

FIELD OF INVENTION

This invention relates to the stimulation of nerves with invasive electrodes for targeted therapeutic interventions.

BACKGROUND

Nerve stimulators commercially available for targeted nerve therapies are exemplified by the NeuroTrace III (HDC Corp., Milpitas, Calif.), the Stimuplex (B. Braun America, Bethlehem, Pa.) and the Digistim III (NeuroTechnologies, Inc, Chennai, India), among others. These devices are constant current, monophasic, pulsed square waveform generators having pulse widths no longer than 200 microseconds in duration. These devices are connected to insulated hypodermic needles which are inserted through the skin and advanced toward the presumed position of a target nerve. Accurate localization of the needle tip is presumed when either a sensory paresthesia or a motor paresthesia is provoked by current outputs less than 0.5 mA. This work is derived from historical strength-duration curves. However, there are several problems with these devices.

The following references will be used to discuss relevant prior art and inadequacies.

1. Cooper M S. Membrane Potential Perturbations Induced in Tissue Cells by Pulsed Electric Fields. *Bioelectromagnetics* 1995; 16:255–62.
2. Vloka J D and Hadzic A. The Intensity of the Current at Which Sciatic Nerve Stimulation Is Achieved Is More Important Factor in Determining the Quality of Nerve Block That the Type of Motor Response Obtained. *Anesthesiology* 1998; 88(5):1408–10.
3. Barthram C N. Nerve Stimulators for Nerve Location— Are They All the Same? *Anaesthesia* 1997; 52:761–4.
4. Pither, C. E., Raj, P. P., and Ford, D. J. The Use of Peripheral Nerve Stimulators for Regional Anesthesia: A Review of Experimental Characteristics, Technique and Clinical Applications. *Reg Anesth* 1985; 10(2):49–58.
5. Andres, J. D. and Sala-Blanch, X. Peripheral Nerve Stimulation in the Practice of Brachial Plexus Anesthesia: A Review. *Reg Anesth Pain Med* 2001; 26(5):478–83.
6. Hadzic A; Vloka J, Hadzic N, Thys D M, Santos A C. Nerve stimulators used for peripheral nerve blocks vary in their electrical characteristics. *Anesthesiology* 2003; 98(4): 969–74.
7. Urmey, W. F. Interscalene Block: The Truth About Twitches. *Reg Anesth Pain Med* 2000; 25(4):340–2.
8. Urmey, W. F.; Stanton, J.; O'Brien, S.; Tagariello, V.; Wickiewicz, T. L. Inability to Consistently Elecit a Motor Response Following Sensory Paresthesia During Interscalene Block Administration. *Reg Anesth* 23, 7. 1998.
9. Choyce A; Chan V W; Knight W J; Peng P; McCartney C J. What is the relationship between paresthesia and nerve stimulation for axillary brachial plexus block? *Reg Anesth Pain Med* 26[2], 100–104. 2001.
10. Hille B. Ionic Basis of Resting and Action Potentials. Brookhart, J. M., Mountcastle, V. B., and Kandel, E. R. *The Nervous System*. Baltimore, Md.: Waverly Press, Inc; 1977. pp. 99–136.
11. Hodgkin A L and Huxley A F. A Quantitative Description of Membrane Current and Its Application to Conduction and Excitation in Nerve. *J Physiol* 1952; 117:500–44.
12. Cole K S, *Membranes, ions, and impulses*. Berkeley and Los Angeles: University of California Press; 1972. (Biophysics Series; 1).
13. Rall W. Core Conductor Theory and Cable Properties of Neurons. Brookhart, J. M., Mountcastle, V. B., and Kandel, E. R. *Handbook of Physiology*, section 1, The Nervous System. Baltimore, Md.: Baltimore, Md.; 1977. pp. 39–97.

Cooper (reference 1 above) developed a mathematical description of the necessary parameters of externally applied, pulsed electric fields for effective nerve stimulation. There are two important concepts that derive from his work. First, an adequate voltage gradient must be generated across the neuronal cell membrane for effective depolarization of the nerve cell to occur. Second, an externally applied electric field must have a pulse duration that is at least 0.5 times the neuronal cell membrane time constant to cause reproducible depolarization.

Anesthesia literature is replete with papers concerning nerve stimulation. In all of these works, the applied current is seen as an important parameter (references 2–9). However, examination of the Hodgkin-Huxley equations reveals that current does not play a role in the opening of membrane sodium or potassium channels. Opening of these channels is required for nerve depolarization to occur (see references 10–12). The role that applied current plays in nerve depolarization is related to the associated voltage gradient required to drive the current through the load represented by the tissue impedance. At a first level approximation, the current to voltage relationship follows Ohm's Law, or $E = I \cdot R$, where E is voltage, I is current, and R is resistance. Clearly, at constant current, the voltage will vary directly with the load. During placement of a needle for nerve stimulation, the load varies with distance from the nerve, as shown by Nervonix experimental data in FIG. 1. Since the impedance decreases as the needle tip approaches the nerve, the applied voltage will also decrease, making the development of an adequate voltage gradient for depolarization unpredictable.

An additional factor in achieving adequate voltage with constant current output is the resistance/capacitance (RC) nature of tissue. Tissue can be represented in equivalent electrical circuits as an RC circuit. When any RC circuit is exposed to a constant current pulse, the associated voltage shows a charging curve as depicted from Nervonix experimental data in FIG. 2. A constant current pulse was directed across tissue via a 22 G insulated needle or a 24 G insulated needle. These data demonstrate that the applied voltage only reaches its maximum toward the end of the 2.5 ms pulse. If the pulse had ended at 0.2 ms, as the commercially available nerve stimulators provide, the voltage would be well short of its maximum value.

Finally, there are a many references regarding the time constant of motoneurons. Rall (reference 13) summarizes these studies, which show that motoneuron membrane time constants range from 3 ms to 7 ms. Based on Cooper's work, if a pulse is to be of adequate duration to reproducibly cause neuronal cell depolarization, it must be greater than 1.5 ms. The commercially available nerve stimulators operate well below this level.

SUMMARY OF THE INVENTION

As with a conventional nerve stimulator, this invention uses a percutaneous needle electrode for the performance of therapeutic interventions targeting nerves. The needle is insulated from the patient except at the tip of the needle, which is to be inserted to within a millimeter or so of a nerve or nerve plexus. A conventional gel-type ground (return)

electrode is also used superficially, and an electrical waveform is applied between the two electrodes.

This invention presents a device (and the method it implements) to improve the design of the nerve stimulators found in prior art. The improvement comprises offering the option for either constant current or constant voltage, offering a wider choice of waveform parameters controlling a pulse generator, supplying a second (background) waveform, measuring the current and voltage applied to the tissue, computing further electrical characteristics from the measurements, adjusting circuit components to insure that a particular waveform is applied to the tissue between the electrodes, and displaying the measured and computed electrical characteristics of the tissue. In particular, this invention comprises a pulse conditioning circuit and method to ensure that the desired waveform and amplitude actually develops across the electrodes. It also comprises two waveform generators.

This invention provides several objectives and advantages. First, it provides a means of developing a predictable voltage gradient across the neuronal cell membrane. Second, the invention provides a means of maintaining the voltage output despite changes in load. Third, the invention provides a means for delivering an adequate pulse duration for neuronal cell depolarization. Fourth, the invention provides a means for the determination of tissue electrical parameters. Fifth, the invention provides a means for adjusting output characteristics based on measured tissue electrical parameters. The principal advantage of a system satisfying these objects is improved localization of nerves or nerve plexuses for regional anesthesia, pain management, and other medical purposes.

Attaining those objectives will support more accurate positioning of a needle tip in proximity to nerves or nerve plexuses for the following applications:

local anesthetic injection for regional anesthesia purposes;

local anesthetic injection for pain management purposes;

catheter placement for injection purposes; and injection of other agents acting on nerve for therapeutic purposes (i.e. neurotoxins, nerve growth factor, . . . ).

DESCRIPTION OF THE DRAWINGS

The accompanying drawings, which are incorporated herein and form a part of the specification, illustrate a preferred embodiment of the present invention and, together with the description, serve to explain the principle of the invention.

DETAILED DESCRIPTION OF A PREFERRED EMBODIMENT

Figure 3:
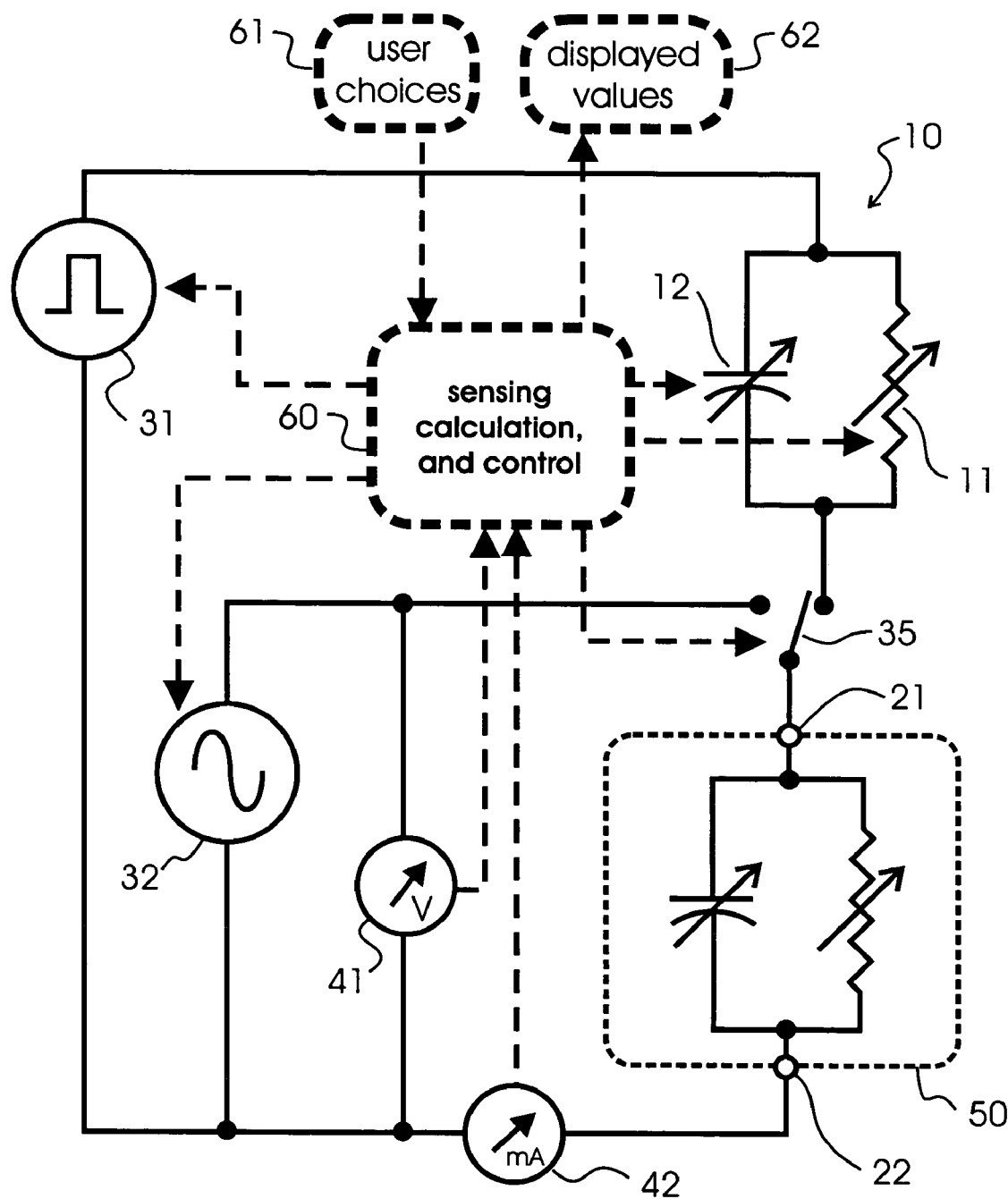
FIG. 3 is a schematic diagram of the electronic circuitry and of the data and control paths of a means to measure and compute electrical characteristics and to adjust the circuitry characteristics. This measurement, computation, and adjustment could presumably be automated by computer hardware and software.

A description of the preferred embodiment and some variations will make reference to the schematic diagram in FIG. 3. The solid lines represent electronic circuitry. The dotted box 50 represents the nerve-containing tissue and encloses an equivalent resistance and capacitance between the needle electrode 21 and the return electrode 22. The tissue resistance and capacitance vary, as the needle is advanced through the tissue—presumably toward a nerve.

The circuitry comprises two waveform generators 31 and 32, a pulse conditioning circuit 10 with a variable resistor 11 and a variable capacitor 12, a switch 35 which connects one of the two generators at a time into the circuitry, a percutaneous needle electrode 21, a ground electrode 22, and sensors 41 and 42 to measure electrical characteristics such as instantaneous voltage and current between the electrodes in real time. Resistor-capacitor (RC) circuit 50 represents the effective electrical characteristics of the tissue conducting the waveform developed between the electrodes 21 and 22.

The dashed lines represent data acquisition, calculation, and control of variable elements of the circuitry. Although the dashed lines could represent manual operation by a human user, the intent of this invention is to automate the broken-line portion of FIG. 3 with the hardware and software of a digital computer. The digital computer might include a conventional laptop computer with hardware input/output interfaces, or it may be a completely custom system. In any case the acquisition and control form a controlled feed-back system, which can measure the voltage 41 across the electrodes 21 and 22 and the current 42 through them. In response, it can control the two waveform generators 31 and 32, the capacitance 12 and resistance 11 values of the pulse conditioning circuit 10, and the selection and duration of the applied waveforms by means of switch 35.

The needle electrode 21 may be any commercially available needle for use with traditional nerve stimulators. They insulate the electrode from the tissue of the patient except at the tip of the needle 21. The return (ground) electrode 22 may also be a conventional gel-type electrode, preferably located approximately 20 centimeters away from the anatomical location of the needle.

Figure 1:
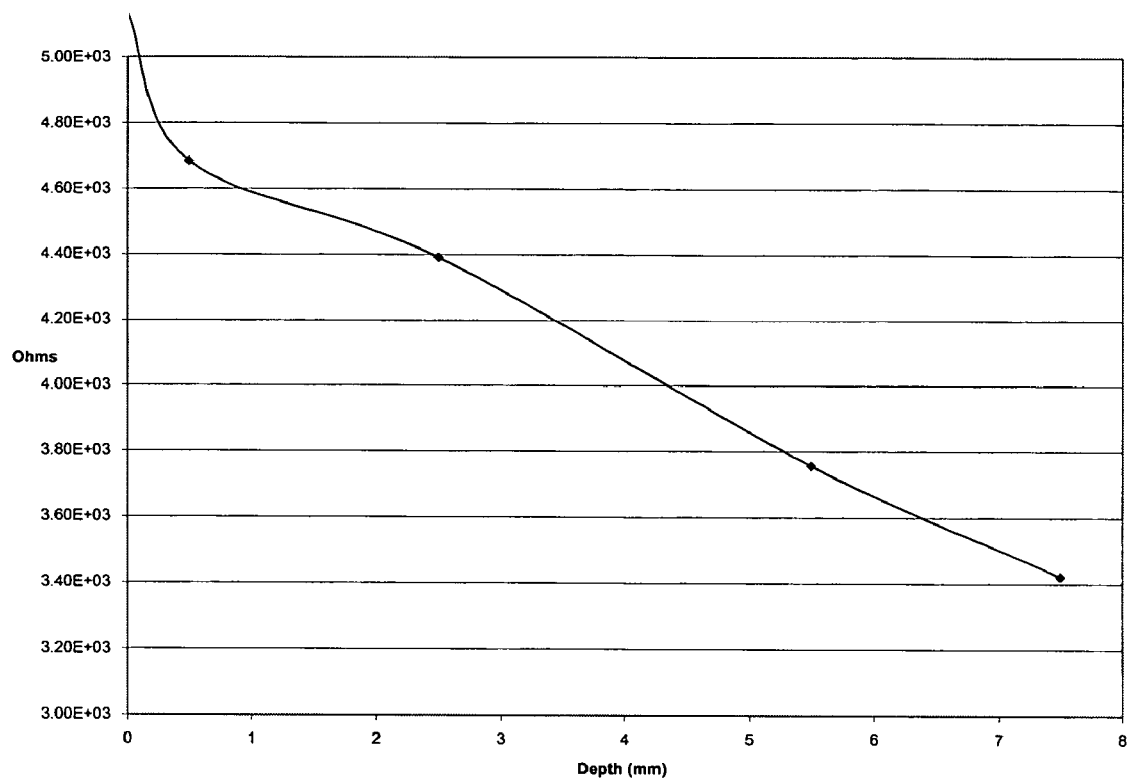
FIG. 1 graphs empirical impedances for a 24 G Stimuplex insulated needle at various needle tip depths using 40 microampere constant current output. Nerve position was determined to be 7.5 mm below the skin surface.
Figure 2:
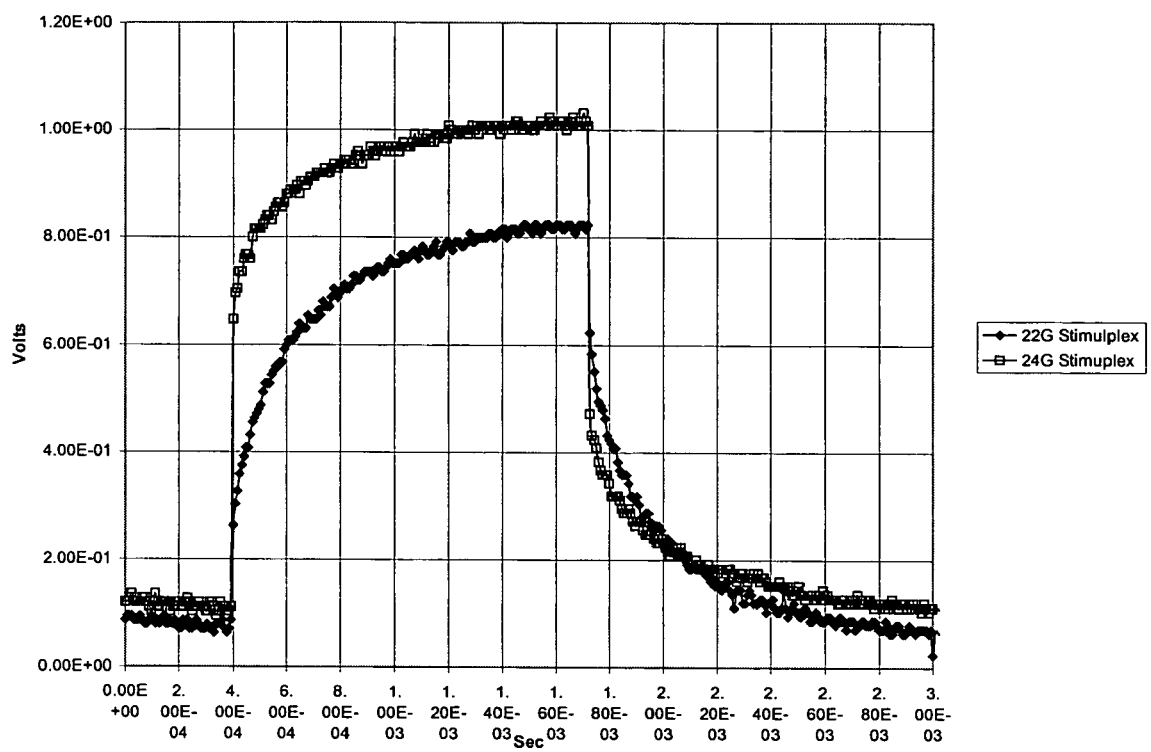
FIG. 2 graphs empirical voltages of a 48 microampere, 2.5 millisecond, square wave output across subcutaneous, 22 G and 24 G Stimulplex needles with a return (ground) electrode at a distance of about 20 centimeters.

An important aspect of the present invention is the pulse conditioning circuit 10 in series with the electrical path through the tissue 50. Waveform generator 31 applies a waveform across this combination circuit. Pulse conditioning circuit 10 is shown simply as a variable resistor 11 and variable capacitor 12 in parallel, although a more complex circuit employing active semiconductor components would likely be used. Pulse conditioning circuit 10 affects the waveform and is intended to introduce circuit characteristics so that the waveform across the electrodes approximates a desired waveform—such as a square pulse, unlike FIG. 2. The components of the pulse conditioning circuit 10 are adjustable, so that as the needle electrode 21 penetrates tissue 50 and the effective electrical characteristics of the tissue therefore change, the characteristics of pulse conditioning circuit 10 can be adjusted to maintain the desired waveform across the electrodes 21 and 22.

Note that a waveform includes both voltage and current components, which can be out of phase in a circuit with reactive impedance. Furthermore, the voltage and current may not be linearly related as the tissue impedance changes with needle insertion and because of non-linear impedance characteristics of neurons. Therefore, in a digital implementation, the waveform may be frequently sampled and represented by a sufficiently complete, discrete sequence of voltage and current values. From them the impedance of the circuit can be computed. Alternatively, analog circuits may simply measure the minimum and maximum (or perhaps the average or root-mean-square) values of voltage or current, and from that the impedance can be derived using well-known electronics formulas. The impedance of pulse conditioning circuit 10 at a particular setting may be represented as a complex number representing the combined effects of resistance and reactance. Similarly the effective immediate impedance of the tissue between the electrodes is also a complex value, which changes as the needle electrode is advanced.

The parametric characteristics of pulse conditioning circuit 10 and of the generators 31 and 32 may be adjusted manually by the operator of the device. In that case the dashed lines of FIG. 3 represent the device's operation by a human being. However, it is preferred that such operation be automated by a controller 60, which is a digital computer. The computer would input user choices 61 and a sequence of real-time voltage and current measurements 41 and 42, calculate other circuit characteristics from those measurements, derive the current and voltage waveforms, and adjust pulse conditioning circuit 10 appropriately to maintain the desired complex waveform. Furthermore, controller 60 would adjust the shape and amplitude of the waveforms generated by generators 31 and 32 as well as their duration and selection by means of switch 35. At least some of that information 62 would be displayed for use by the medical practitioner inserting the needle electrode 21. In this case the variable resistor 11, the variable capacitor 12, and the switch 35 likely would comprise solid state electronically varied components.

Therefore, if the pulse waveform generator 31 is a constant current source, pulse conditioning circuit 10 can be adjusted to produce a waveform across the electrodes which approximates a square voltage waveform. Also, pulse generator 31 can be adjusted to produce the desired amplitude. The rationale for this is to maintain a sufficient and fixed voltage differential between the electrodes during the stimulation pulse.

The invention would provide an adjustable voltage range for pulse generator 31 which preferably would include the voltages from 0 up to 24 volts. The current range would preferably include currents from 0 to at least 5 milliamperes. The settings for pulse generator 31 would preferably include a repetition frequency range of 1 to 5 Hertz and a pulse duration of 0.1 to 3 milliseconds.

Figure 4:
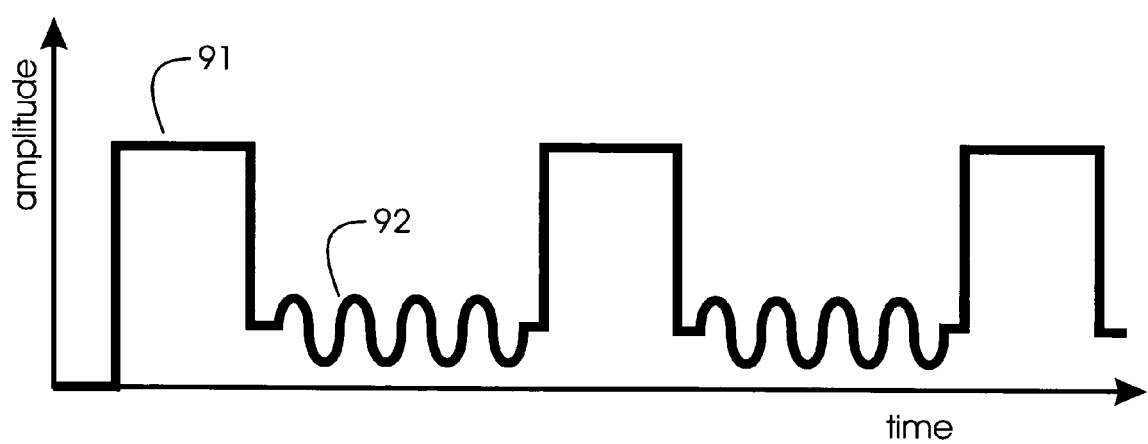
FIG. 4 depicts a representative graph of the amplitude of the voltage applied across the electrodes (or, alternatively, current through the tissue).

The device of this invention further comprises a second (background) waveform generator 32. It produces a periodic waveform, such as a sinusoidal wave, which is applied directly between the electrodes during the interval between the pulses generated by pulse generator 31. Although switch 35 could be manually controlled to select which of generators 31 or 32 is actively connected, the invention preferably employs a solid state switch electronically activated by computer-based control function 60. For this preferred embodiment, it is assumed that the background waveform is applied to the electrodes when and only when the pulse generator is generating zero or minimum amplitude. This is depicted in FIG. 4, which shows waveform 91 generated by the pulse generator 31 and waveform 92 generated by the background (or secondary) generator. Of course, other ways of combining the waveforms are possible, including adding them or providing a period when neither is applied to the electrodes.

As suggested in FIG. 3, the amplitudes and frequencies of both waveform generators 31 and 32 can be adjusted by the operator or can be set by control function 60. Additionally, the user can opt whether each generator sources a current waveform or a voltage waveform. (Herein define the selected amplitude as the peak-to-peak amplitude, although it could be the peak amplitude or root-mean-square amplitude instead.) Furthermore, the pulse width (duration) of the output pulse of generator 31 can be set. A more sophisticated variation of this embodiment would also allow the user (or control function 60) to control the shapes of each of the waveforms output by generators 31 and 32.

The secondary (background) generator 32 would preferably use a constant current output with a selectable frequency in a preferred range of 500 to 10000 Hertz. Current would be limited to 100 microamperes. The purpose of the second (background) waveform generator is to allow a more passive detection of the proximity of a nerve or nerve plexus without explicitly stimulating the nerve above activation threshold.

FIG. 3 further depicts a voltmeter 41 and an ammeter 42 at preferred locations. Of course, other such sensors could be deployed in other parts of the circuitry. These could be analog or digital devices. They could each provide human-oriented readouts. More preferably the sensors would be analog-to-digital converters connected as digital inputs to a computerized controller 60. A current-measuring sensor would undoubtedly be a voltage sensor wired across (in parallel with) a low-resistance precision resistor.

Internal details for the waveform generators 31 and 32 are ignored here, because circuits for various kinds of current-controlled or voltage-controlled waveform generators are well known to those with reasonable skill in electronics. Similarly, circuits for electronic switch 35 and for measuring voltage 41 and current 42 are well known.

While this invention is described above with reference to a preferred embodiment, anyone skilled in the art can readily visualize alternative embodiments of this invention. Therefore, the scope and content of this invention are not limited by the foregoing description. Rather, the scope and content are delineated by the following claims.

I claim:

1. A device for improved nerve stimulation via a percutaneous insulated needle for the performance of therapeutic interventions targeting nerves within living tissue, comprising:

a needle electrode which is configured to be used percutaneously and is insulated except at a tip;

a return electrode;

a pulse generator;

a background waveform generator;

a switch electrically connected to the pulse generator and the background waveform generator and configured to connect one of the pulse generator and the background waveform generator at a time to the needle electrode and the return electrode;

a pulse conditioning circuit electrically connected in series with an electrical path created through tissue between the needle and the return electrodes when the needle electrode and the return electrode are applied to tissue;

sensors electrically connected to the needle electrode and the return electrode and configured to detect electrical characteristics of the waveforms generated by the pulse and background waveform generators; and a controller configured for acquiring user parameter choices, for acquiring real-time measurements of the pulse and waveform, for calculating other waveform characteristics from the measurements, for calculating tissue characteristics from the waveform characteristics, and for adjusting parametric characteristics of the pulse generator, the background waveform generator and the conditioning circuit, to produce a desired waveform across the electrodes and to generate various measured and calculated values for the benefit of a practitioner when the needle electrode is advanced into the tissue;

wherein the controller is programmed to adjust the parametric characteristics of the pulse and background waveform generators and the conditioning circuit in order to produce a desirable waveform across the electrodes by sampling the electrical characteristics of the waveforms using the sensors.

2. The device of claim 1, wherein the return electrode is a superficial, gel electrode.

3. The device of claim 1, wherein the pulse generator maintains an adjustable, specified current amplitude level across a varying impedance.

4. The device of claim 3, wherein the current amplitude level of the pulse generator may be in the range of 0 to 5 milliamperes.

5. The device of claim 1, wherein the pulse generator operates at a pulse frequency between 1 and 5 Hertz.

6. The device of claim 1, wherein the pulse generator generates square wave pulses.

7. The device of claim 6, wherein the pulse generator generates pulses with a duration of 0.1 to 3 milliseconds.

8. The device of claim 1, wherein the frequency of the background generator may be selected from within a range of 500 to 10000 Hertz.

9. The device of claim 1, wherein the background waveform generator generates a waveform with a specified current amplitude across a varying impedance.

10. The device of claim 1, the output of the background waveform generator has a maximum current of 100 microamperes.

11. The device of claim 1, wherein the output of the background generator is directed across the electrodes.

12. The device of claim 1, wherein the output of the background generator is a sinusoidal waveform with a constant offset.

13. The device of claim 1, wherein the pulse conditioning circuit comprises a capacitor in parallel with a resistor.

14. The device of claim 1, wherein the pulse conditioning circuit includes a variable capacitor.

15. The device of claim 1, wherein the pulse conditioning circuit includes a variable resistor.

16. The device of claim 1, wherein a sensor utilizes an analog-to-digital converter.

17. The device of claim 1, wherein a sensor measures the real-time current at least 10 times faster than the highest frequency of the generators and with at least 8 bits of digital resolution.

18. The device of claim 1, wherein the waveform of the background generator is maintained at a specified current amplitude.

19. The device of claim 1, wherein the controller is a programmed electronic computer with digital inputs and outputs.

20. The device of claim 1, wherein a display graphs the shape of the waveform applied across the electrodes.

21. The device of claim 1, which further comprises an indicator, which indicates the proximity of the tip of the needle electrode to a nerve.

22. The device of claim 21, wherein the indicator generates an audible tone.

23. The device of claim 21, wherein the indicator is a visual display.

24. The device of claim 23, wherein the visual display displays the waveform voltage.

25. The device of claim 23, wherein the visual display displays the waveform current.

26. The device of claim 23, wherein the visual display displays the calculated impedance of the tissue between the electrodes.

27. The device of claim 23, wherein the visual display displays the pulse duration.

28. The device of claim 23, wherein the visual display displays the frequency of the pulses.

29. The device of claim 21, wherein the indicator indicates an error status.

30. A device for improved nerve stimulation via a percutaneous insulated needle for the performance of therapeutic intervention targeting nerves within living tissue, comprising:

a needle electrode which is configured to be used percutaneously and is insulated except at a tip;

a return electrode;

a pulse generator;

a background waveform generator;

a switch electrically connected to the pulse generator and the background waveform generator and configured to connect one of the pulse generator and the background waveform generator at a time to the needle electrode and the return electrode;

a pulse conditioning circuit electrically connected in series with an electrical path created through tissue between the needle and the return electrodes when the needle electrode and the return electrode are applied to tissue;

sensors electrically connected to the needle electrode and the return electrode and configured to detect electrical characteristics of the waveforms generated by the pulse and background waveform generators; and a controller configured for acquiring user parameter choices, for acquiring real-time measurements of the pulse and waveform, for calculating other waveform characteristics from the measurements, for calculating tissue characteristics from the waveform characteristics, and for adjusting parametric characteristics of the pulse generator, background waveform generator and the conditioning circuit, to produce a desired waveform across the electrodes and to generate various measured and calculated values for the benefit of a practitioner when the needle electrode is advanced into the tissue, wherein:

the controller is programmed to adjust the parametric characteristics of the pulse and background waveform generators and the conditioning circuit in order to produce a desirable waveform across the electrodes by sampling the electrical characteristics of the waveform using the sensors; and the pulse generator maintains an adjustable, specified voltage amplitude level across a varying impedance.

31. The device of claim 30, wherein the wherein the voltage amplitude level of the pulse generator may in the range of 0 to 24 volts.

32. The device of claim 30, wherein a sensor measures the real-time voltage at least 10 times faster than the highest frequency of the generators and with at least 8 bits of digital resolution.

33. The device of claim 30, wherein the waveform of the background generator is maintained at a specified voltage amplitude.

34. A method of improved nerve stimulation via a percutaneous insulated needle for the performance of therapeutic interventions targeting nerves within living tissue, comprising steps of:
- attaching a return electrode;
- inserting a needle electrode percutaneously into tissue, where the needle electrode is insulated from the tissue except at the tip of the electrode;
- adjusting the characteristics of a pulse conditioning circuit in series with the electrical path between the two electrodes through the tissue;
- applying a pulse waveform of a specified shape and specified amplitude to the electrodes;
- measuring an electrical characteristic of the waveform applied to the electrodes;
- calculating a tissue characteristic based on the measured electrical characteristic of the waveform; and
- displaying a location of a nerve.

35. The method of claim 34, wherein the return electrode is a superficial gel electrode.

36. The method of claim 34, wherein the pulse conditioning circuit comprises a capacitor in series with a resistor.

37. The method of claim 34, wherein adjusting the characteristics of a pulse conditioning circuit comprises adjusting a variable capacitor within the pulse conditioning circuit.

38. The method of claim 34, wherein adjusting the characteristics of a pulse conditioning circuit comprises adjusting a variable resistor within the pulse conditioning circuit.

39. The method of claim 34, wherein the specified shape is a square wave.

40. The method of claim 34, wherein the specified amplitude is a current amplitude across a varying impedance.

41. The method of claim 34, wherein the specified amplitude is a voltage amplitude across a varying impedance.

42. The method of claim 34, wherein a pulse generator applies a waveform across a series circuit comprising the pulse conditioning circuit and the tissue between the electrodes.

43. The method of claim 34, wherein the calculating step computes the total impedance of the tissue.

44. The method of claim 34, wherein the calculating step computes the resistance and reactance of the impedance of the tissue.

45. The method of claim 34, further comprising displaying tissue impedance.

46. The method of claim 34, further comprising displaying values of the measured electrical characteristic.

47. The method of claim 34, wherein the displaying step displays the estimated distance to the nerve.

48. The method of claim 34, further comprising displaying the shape of the waveform applied across the electrodes.

* * * * *